United States Patent [19]

Taillandier et al.

[11] 4,025,649

[45] May 24, 1977

[54] ACETIC ACID DERIVATIVES HAVING PHARMACOLOGICAL ACTIVITY AND COMPOSITIONS CONTAINING THE SAME

[75] Inventors: Georges Marcel Taillandier; Jean-Louis Alain Benoit-Guyod, both of Grenoble; Andre Louis Boucherle, Corenc-Montfleury; Pierre Luc Eymard, Fontaine; Madeleine Broll, Grenoble; Bernard Ferrandes, Claix, all of France

[73] Assignee: Labaz, Paris, France

[22] Filed: June 18, 1975

[21] Appl. No.: 588,001

[30] Foreign Application Priority Data

June 26, 1975 France .................. 75.28416

[52] U.S. Cl. .................. 424/318; 424/317
[51] Int. Cl.² .................. A61K 31/19; A61K 31/20
[58] Field of Search .................. 424/317, 318

[56] References Cited

UNITED STATES PATENTS 2,484,486 10/1949 Caldwell .................. 260/540
2,484,500 10/1949 Hagemeyer .................. 260/540

Primary Examiner—Frederick E. Waddell

Attorney, Agent, or Firm—Mason, Kolehmainen, Rathburn & Wyss

[57] ABSTRACT

Acetic acid derivatives of the formula:

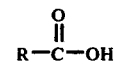

and pharmaceutically acceptable alkali metal salts thereof, wherein R represents the radical

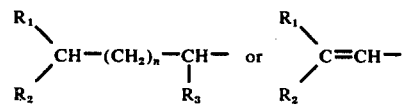

in which $R_1$ and $R_2$, which may be the same or different, each represent an alkyl radical having from 1 to 4 carbon atoms, $R_3$ represents a hydrogen atom or a methyl radical and $n$ is an integer in the range of from 0 to 3 inclusive.

They possess a competitive inhibitory activity with respect to γ-aminobutyric α-ketoglutaric transaminase as well as antianoxic and anticonvulsant properties and they are useful for treating central neurological disorders whether resulting or not from cerebral ischemia.

13 Claims, No Drawings

ACETIC ACID DERIVATIVES HAVING PHARMACOLOGICAL ACTIVITY AND COMPOSITIONS CONTAINING THE SAME

This invention relates to acetic acid derivatives having pharmacological activity, to pharmaceutical and veterinary compositions containing them and to a process for preparing these derivatives and compositions.

The pharmacologically active compounds with which the present invention is concerned are the acetic acid derivatives represented by the general formula:

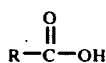

wherein R represents the radical

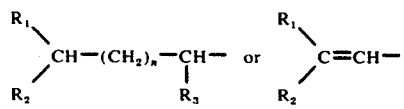

in which $R_1$ and $R_2$, which may be the same or different, each represent an alkyl radical having from 1 to 4 carbon atoms, $R_3$ represents a hydrogen atom or a methyl radical and $n$ is an integer in the range of from 0 to 3 inclusive, as well as the pharmaceutically acceptable alkali metal salts of these compounds.

In accordance with another aspect of the invention there is provided a pharmaceutical or veterinary composition comprising, as an essential active ingredient, at least one acetic acid derivative of formula I, or a pharmaceutically acceptable alkali metal salt thereof, in association with a pharmaceutical carrier or excipient therefor.

A further object of the invention is to provide a process for preparing pharmaceutical or veterinary compositions whereby at least one acetic acid derivative such as defined in formula I or a pharmaceutically acceptable alkali metal salt thereof is associated with an appropriate pharmaceutical carrier or excipient.

As will be described in greater detail further on, it has been found that the acetic acid derivatives of the invention are endowed with biochemical and pharmacological properties likely to render them particularly useful in the treatment of pathological conditions due to disturbances of the central nervous system.

Pharmacological and biochemical tests have shown that the compounds of the invention can act as competitive inhibitors with respect to the action of γ-aminobutyric α-ketoglutaric transaminase and also as anticonvulsant and antianoxic agents.

Consequently, the compounds of the invention will constitute particularly valuable agents for treating various kinds of central neurological disorders whether resulting or not from cerebral ischemia.

Hence, another object of the invention is to provide a method of treating central neurological disorders whether resulting or not from cerebral ischemia and including, in particular, convulsive states and seizures, in a host in need of such treatment, such method comprising the administration to said host of an effective dose of at least one acetic acid derivative of formula I or a pharmaceutically acceptable alkali metal salt thereof.

Daily dosage will preferably be between 400 and 2000 mg of active principle by any route for a human being weighing 60 kg, for example about 1000 mg by oral or rectal route.

Amongst the compounds of formula I, a certain number are known products. In this connection may be cited:

3-Methyl-butanoic acid, 3-methyl-pentanoic acid and 4-methylpentanoic acid which are cited in U.S. Pat. No. 2,484,486. Furthermore, this same U.S. Patent also generically covers the whole of the compounds of formula I wherein R represents

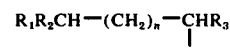

in which $R_1$ and $R_2$ have the same meaning as in formula I, $R_3$ represents hydrogen and $n$ is 0.

3-Ethyl-pentanoic acid and 3-ethyl-2-pentenoic acid which are described in Berichte 42, 4710-4713.

3-n-Propyl-hexanoic acid which is cited in Chem. Abstracts, 35, 47336 (1941).

4-n-Propyl-heptanoic acid which is mentioned in Ann. Chem. 693, 90-98 (1966).

5-n-Propyl-octanoic acid which is disclosed in Physiol. Chem. 282, 135-142 (1947).

3-n-Propyl-2-hexenoic acid and 3-isobutyl-5-methyl-2-hexenoic acid which are described in J. Chem. Soc., 129, 1549-1555 (1927).

The compounds of formula I in which R represents

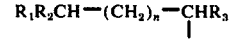

wherein $R_1$ and $R_2$ each represent methyl or ethyl and $R_3$ represents methyl with $n$ equal to 0 which are covered by U.S. Pat. No. 2,484,500.

However, as far as is known, no therapeutic activity has ever been attributed to these compounds of formula I cited hereabove with the exception of 3-methyl-pentanoic acid which is included in the composition of officinal valerianic acid known for its sedative properties [MERCIER, Les Medicaments du systeme nerveux cerebro-spinal p. 171 (1959)].

The other compounds of formula I can be considered as novel products. In fact, searches have not revealed any publication with respect to these other acids of formula I.

Similarly, the pharmaceutically acceptable alkali metal salts of the compounds of formula I can also be regarded as novel compounds.

In consequence, the invention also relates, as new compounds, to the pharmaceutically acceptable alkali metal salts of the compounds of formula I and more particularly, as preferred compounds, to the pharmaceutically acceptable alkali metal salts corresponding to the general formula:

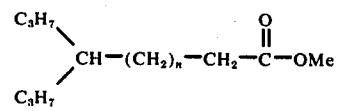

wherein Me represents an alkali metal atom, for example lithium, sodium or potassium, and $n$ is an integer in the range of from 0 to 2 inclusive.

The compounds of the invention can be obtained by various procedures in accordance with their chemical structure.

Thus, the compounds of formula I wherein R represents

may be prepared as follows:

a. When $n$ is 0, by hydrogenating in an appropriate solvent such as for example absolute ethanol and in the presence of a catalyst such as for example Raney's nickel, a mixture of ethylenic acids obtained by dehydrating, for example with acetic anhydride, a $\beta$-hydroxy acid of the general formula:

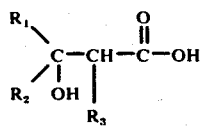

wherein $R_1$, $R_2$ and $R_3$ have the same meaning as in formula I, which provides the required compound of formula I in free acid from which, if desired, can be treated by means of an alkali metal hydroxide, for example lithium, sodium or potassium hydroxide, to obtain the corresponding pharmaceutically acceptable alkali metal salt thereof. The hydrogenation is carried out under pressure and by heating the mixture of ethylenic acids in question and the dehydration is preferably effected by heating the reagents.

b. When $n$ is 1 to 3 by oxydizing, for example by means of chromic anhydride, in an appropriate solvent such as for example acetic acid, an alcohol of the general formula:

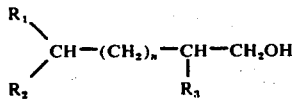

wherein $R_1$, $R_2$ and $R_3$ have the same meaning as in formula I and $n$ is an integer in the range of from 1 to 3 inclusive, to obtain the required compound of formula I in free acid form which, if desired, can be treated by means of an alkali metal hydroxide, for example lithium, sodium or potassium hydroxide, to form the corresponding pharmaceutically acceptable alkali metal salt thereof.

The compounds of formula I wherein R represents $R_1R_2C=CH-$ can be obtained by dehydrating, for example by means of acetic anhydride, the appropriate $\beta$-hydroxy acid derivative of formula II, corresponding to the general formula:

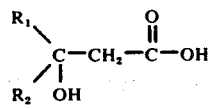

wherein $R_1$ and $R_2$ have the same meaning as in formula I, to form the required compound of formula I in free acid form which, if desired, can be treated by means of an alkali metal hydroxide, for example lithium, sodium or potassium hydroxide, to obtain the corresponding pharmaceutically acceptable alkali metal salt thereof.

The dehydration may be effected by heating the reagents for example under reflux.

The compounds of formula II can be prepared by reacting a dianion obtained from an aromatic hydrocarbon such as naphtalene or anthracene, an alkali metal such as lithium, sodium or potassium and an acid of the general formula:

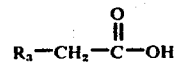

wherein $R_3$ has the same meaning as in formula I with a ketone of the general formula:

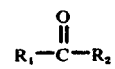

wherein $R_1$ and $R_2$ have the same meaning as in formula I in an anhydrous ether such as ethyl ether, hydrolysing the alkali metal salt so obtained and subsequently acidifying the salt to form the required $\beta$-hydroxy acid derivative. All the acids of formula V and ketones of formula VI are known and commercialized compounds.

Similarly, the compounds of formula III are either known compounds or can be prepared by the method described in Ann. Chem. 1966, 693, 90–98.

As already mentioned, the compounds of the invention have been found to possess valuable biochemical properties, and in particular a marked competitive inhibitory effect with respect to the action of $\gamma$-aminobutyric $\alpha$-ketoglutaric transaminase. The compounds of the invention also possess powerful pharmacological activity and more particularly marked antianoxic and anticonvulsant properties.

These properties, when taken as a whole, are likely to render the compounds of the invention useful for treating various kinds of central neurological disturbances whether resulting or not from cerebral ischemia.

As an example of such central neurological disturbances or of disorders induced by central neurological dysfunction, the following may be cited: convulsive states and seizures such as, for example, epilepsy, choreic states such as Huntington's chorea, difficulties with respect to memory, balance and fixing the attention, as well as dizziness, decrease of arterial pressure, cephalalgia and comatose states.

$\gamma$-Aminobutyric acid or GABA is an important constituent of the brain of the vertebrates. At present, it represents the only known physiological inhibitor of the pre- and postsynaptic discharges which it has been possible to isolate in the brain. Furthermore, this acid plays an all important role in the case of choreic patients in whom cerebral depletion in GABA has been observed.

The normal oxidative metabolism of the carbohydrates leads in particular to the production of $\alpha$-ketoglutaric acid through the medium of the tricarboxylic cycle of KREBS. From this point a deviation occurs which results in the formation of GABA.

Various enzymes regulate by natural processes the production and destruction of this acid and of GABA itself which is re-transformed into $\alpha$-ketoglutaric acid, this latter acid being taken up again in the KREBS' cycle. The activity of these enzymes can itself be either accelerated or inhibited by several substances.

It has been discovered, in accordance with the invention, that the acetic acid derivatives of the invention are capble of producing a competitive inhibitory effect with respect to the action of γ-aminobutyric α-ketoglutaric transaminase or GABA T which destroys GABA. Such an inhibitory effect consequently produces an increase in the GABA level in the organism.

These biochemical properties are likely to produce more particularly an anticonvulsant action in pharmacology and in clinical use to exert antiepileptic and antichoreic effects.

Furthermore, the compounds of the invention have been found to be strong antianoxic agents capable in particular of delaying the onset of cerebral pain due to oxygen deficiency i.e. originating from cerebral ischemia.

Cerebral ischemia can be provoked by numerous factors such as, for example: cerebral vascular deficiency due to senescence, thrombosis or tumors. At present cerebral vasodilators are commonly used in order to delay the onset of cerebral pain due to oxygen deficiency or to treat cerebral vascular deficiency and its resulting disorders for example central neurological disturbances such as those cited hereabove.

However, such drugs must be employed in accordance with the vascular state of the patient. Since these compounds act by mechanical means, namely by dilating the arterioles to increase the blood flow and consequently the amount of oxygen in the brain, they will be ineffective, for example in cases involving arteriosclerosis.

Furthermore, certain agents can provoke a marked cerebral vasodilation of the healthy parts which upsets the circulatory equilibrium. As a consequence of this, a decrease of irrigation in the ischemic parts can occur.

The compounds of the invention on the other hand do not present these disadvantages as they do not act by mechanical means by exert their effect directly on the metabolism of the nervous cells without affecting, the conditions of irrigation. They do, in fact, act by bringing about an economy and a better use of oxygen in the nervous cells. These antianoxic properties will also be useful for preventing convulsive seizures as it is well known that anoxia can induce such seizures.

In the light of these different properties, the compounds of the invention will be likely to constitute valuable antianoxic agents, for example, for treating central neurological disturbances due to cerebral ischemia, particularly in cases where the classic drugs are ineffective.

In the field of diseases requiring anticonvulsant therapy and, in particular, epilepsy, there are numerous drugs of undeniable efficacy. However, these classic medicaments, such as the barbiturates and molecules of similar structure cause an overall depression of the central nervous system, which moreover, explains their anticonvulsant effect.

For this reason, such drugs frequently cause undesirable side-effects such as difficulty in fixing the attention, reduction in intellectual efficiency and somnolence as well as biological disorders of which the most serious are hematological.

The compounds of the invention do not present these disadvantages since they do not act by provoking a general depression of the central nervous system but, on the contrary, they function by means of an enzymatic mechanism involving the metabolism of a neurotransmittor which is a physiological inhibitor namely γ-aminobutyric acid. Furthermore, certain well-known anticonvulsant agents are toxic at relatively low doses while others are only useful for the treatment of one single type of epilepsy.

The compounds of the invention do not present these disadvantages since they are relatively non-toxic and at the same time possess a very wide range of properties which are likely to render them useful in the treatment of an extremely broad variety of convulsive states.

Compounds of a similar chemical structure to that of the compounds of the invention, namely dialkylacetic acid derivatives which possess anticonvulsant properties have been published in U.S. Pat. No. 3,325,361. A detailed study has been carried out with sodium di-n-propylacetate which is the preferred compound of the above-cited U.S. Patent.

This study, which is reported in J. of Neurochemistry, 1969, Vol. 16, pp. 869–873, showed that sodium di-n-propylacetate is capable of increasing the level of intracerebral GABA by inhibiting GABA T. Up to present, no other therapeutic substance is known which possesses this property. This property endows sodium di-n-propylacetate with powerful anticonvulsant activity and a completely original mechanism of action.

Similarly, it has been demonstrated, as reported in Bull. Soc. Sci. Vet. et Med. comparee, Lyon, 1970, 72, pp. 303–325, that sodium di-n-propylacetate possesses very marked antianoxic properties.

At present, sodium di-n-propylacetate is widely commercialized as an antiepileptic agent.

However, it has been discovered in accordance with the present invention that the acetic acid derivatives of formula I as well as their pharmaceutically acceptable alkali metal salts, possess the above-cited properties of sodium di-n-propylacetate but to different degress which confer on them an originality of action as compared with this latter product.

Thus, pharmacological tests have shown that at least one of the three biochemical and pharmacological activities cited hereabove is more intense in the case of the compounds of the invention than in that of sodium di-n-propylacetate.

In therapeutic use this essential difference between sodium di-n-propylacetate and the compounds of the invention will be likely to render the latter more selective for the treatment of certain kinds of central neurological disorders whether resulting or not from cerebral ischemia. For example, the compounds of the invention which have been found to be more active than sodium di-n-propylacetate as competitive inhibitors of GABA T will be likely to be more effective, for example, in the treatment of choreic states. On the other hand, the compounds of the invention which have shown better antianoxic properties than sodium di-n-propylacetate will be more active in the treatment of central neurological disorders due to cerebral ischemia.

Disturbances and dysfunction of the central nervous system whether of ischemic origin or not are numerous and constitute one of the most widespread disorders at the present time.

For this reason, it is very difficult for the doctor to choose amongst the various drugs at his disposal, that which will be effective for the particular case under treatment. When faced with a case of chorea, epilepsy or other affection, the neurologist is often obliged to feel his way by trying several drugs one after the other until he discovers the most suitable medication.

From this point of view, the compounds of the invention will constitute valuable additions to the therapeutic arsenal at the disposal of the doctor and, if necessary, will provide useful replacement medication for a drug which has become ineffective for any reason such as, for example, a change in the state of the patient or habituation.

The compounds of the present invention which have been found to be particularly useful for the treatment of central neurological disturbances whether originating or not from cerebral ischemia and in particular epilepsy are:
  3-n-Propyl-hexanoic acid
  4-n-Propyl-heptanoic acid and
  5-n-Propyl-octanoic acid
as well as their pharmaceutically acceptable alkali metal salts.

Pharmacological trials have been undertaken with a view to determining the presence of a competitive inhibitory effect with respect to the action of γ-aminobutyric α-ketoglutaric transaminase, as well as antianoxic and anticonvulsant properties which, taken together, are capable of rendering the compounds of the invention useful for treating central neurological disturbances whether originating or not from cerebral ischemia.

I. Inhibition of GABA T.

This test was undertaken "in vitro" in the absorption cell of a double-beam U.V. spectrophotometer.

The activity of GABA T was determined by coupling this enzyme with an excess of succinosemialdehyde dehydrogenase (NADP⁺) so that the rate of formation of the succinosemialdehyde dehydrogenase coenzyme (NADPH) was limited by the activity of the GABA T. The coupling of the two reactions was as follows:

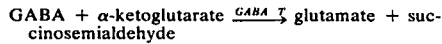
GABA + α-ketoglutarate $\xrightarrow{GABA\ T}$ glutamate + succinosemialdehyde In the presence of succinosemialdehyde dehydrogenase of which the active element is NADP⁺, the reaction became:

succinosemialdehyde + NADP⁺ + H₂O → succinate + NADPH + H⁺

The overeall reaction can be represented by the following equation: GABA + α-ketoglutarate + NADP⁺ + H₂O → succinate + glutamate + NADPH + H⁺

The activity of GABA T was measured by following the reduction rate (v) of NADP⁺ which corresponds to the evolution of the optical density at 340 mμ on the spectrophotometer.

Determination of the activity rate of GABA T by the principle hereabove described can be effected with either limiting concentrations or a saturating concentration of one of the substrates, in the present case GABA, in each instance, in the presence of a saturating concentration of the second substrate namely α-ketoglutarate. Thus, it is possible to discover the activity rate of GABA T in relation to the concentration of GABA and in this way, to determine the affinity of GABA T for GABA.

Similar measurements of the activity of GABA T were then carried out in the presence of different concentrations (I) of an inhibitor namely a compound of the invention, so as to evaluate the effectiveness of the latter. This effectiveness is represented by the constant $K_i$ or constant of inhibition which determines the affinity of the enzyme (GABA T) for the inhibitor.

This constant is expressed in units of concentration, in the present case, in m mole per ml and can be determined by plotting all the curves corresponding to $1/v = f(I)$ for a saturating concentration of GABA and for different limiting concentrations of GABA.

The point of coincidence of these curves determines the $K_i$ in question or the necessary concentration of inhibitor to arrest completely the activity of the GABA T. The lower the $K_i$ value is, the greater is the effectiveness of the inhibition of GABA T by the compound of the invention.

The following experimental procedure was used:

In the absorption cell (optical passage: 1 cm, volume: about 1 ml) the following solutions were introduced.
  0.5 ml of a 1.5 molar solution of sodium sulphate
  0.05 ml of a molar buffer solution of pH = 7.9
  0.05 ml of a 0.1 molar solution of mercapto-ethanol
  0.05 ml of a 20 mg/ml solution of NADP⁺
  0.125 ml of a solution of GABA
  0.03 ml of a 40 mg/ml solution of GABASE (namely a bacterial enzyme isolated from *Pseudomonas fluorescens* containing a mixture of γ-aminobutyric α-ketoglutaric transaminase and succinosemialdehyde dehydrogenase).
  0.125 ml of a solution of the compound to be studied.

If the compound of the invention was in the form of a water-insoluble acid, its sodium salt was used after adjustment to a pH of about 7.9 by adding a titrated solution of sodium hydroxide.

Different measurements of optical density were effected by varying the concentration of GABA and the concentration of the compound under study. Control assays were also effected by replacing the solution of the compound to be studied by 0.125 ml of water.

The content of the absorption cell was allowed to incubate for 10 minutes at 30° C and then the enzymatic reaction was started by adding 0.1 ml of a 0.02 molar solution of α-ketoglutarate in the absorption cell. The final volume was 1.03 ml. The reaction was then followed by spectrophotometric recording of the reduction rate of the NADP⁺ at 340 mμ and at 30° C. The optical density was automatically registered every 30 seconds.

In accordance with the process hereabove described, the following compounds of the invention are studied. These compounds were preferably tested in the form of a pharmaceutically acceptable alkali metal salt, for example the sodium salt.

The pharmaceutically acceptable alkali metal salts of the acids of formula I such as the sodium salt, are in fact more advantageous than the acids themselves. These salts have a much milder irritant effect upon the upper part of the digestive tract than the acids.

Thus, the pharmaceutically acceptable alkali metal salts of the acids of formula I present an undeniable superiority over the corresponding acids.

This will serve to reduce considerably the undesirable side-effects when the salts are used in therapeutics.
  3-n-Propyl-hexanoic acid (Compound A)
  4-n-Propyl-heptanoic acid (Compound B)
  5-n-Propyl-octanoic acid (Compound C)
  3-Methyl-butanoic acid (Compound D)
  3-Ethyl-pentanoic acid (Compound E)

3-n-Butyl-heptanoic acid (Compound F)
3-n-Propyl-2-hexenoic acid (Compound G)

The following $K_i$ were registered with these different compounds of the invention:

TABLE I

| Compound | $K_i$ (in m mol/ml) |
|---|---|
| A | 0.63 ± 0.15 |
| B | 1.05 ± 0.20 |
| C | 1.18 ± 0.50 |
| D | 0.51 ± 0.14 |
| E | 2.15 ± 0.50 |
| F | 1.06 ± 0.58 |
| G | 0.70 ± 0.17 |

A comparative test carried out, under the same conditions with sodium di-n-propylacetate gave a $K_i$ of 0.8 m mol/ml. This result shows that Compounds A, D and G are more active than sodium di-n-propylacetate in this test while Compounds B and F are slightly less active in this test II. Antianoxic activity.

Action on the anoxic seizure induced by gallamine triiodoethylate

The injection of a sufficient dose of a synthetic curariform substance such as gallamine triiodoethylate provokes in the mouse paralysis of the diaphragm. The animal then dies through asphyxia.

An intraperitoneal dose of the compound to be studied was administered to batches of 20 mice five minutes before the administration of 16 mg/kg of gallamine triiodoethylate by intraperitoneal route. The dose of the compound to be tested was calculated so that each batch received a higher dose than the preceding batch.

The period of survival of the treated animals was noted in comparison with that of the controls which had not received the compound under study. The period of time of survival was registered by controlling cardiac arrest by means of an electrocardiogram.

Under these conditions, an antianoxic effect produces an increase in the period of survival of the animal.

The following results were recorded with compounds of the invention :

TABLE II

| Compound | Dose administered in mg/kg | % of increase in the period of survival in comparison with the controls |
|---|---|---|
| A | 360 | 60 |
| D | 250 | 73 |
| E | 150 | 59 |
| F | 210 | 29 |
| G | 355 | 50 |

A comparative trial undertaken with sodium di-n-propylacetate, under the same conditions, showed that a dose of 330 mg/kg of this product increases by 40% the period of survival of the animals in comparison with the controls.

Table II hereabove shows that Compounds D and E are appreciably more active than sodium di-n-propylacetate as antianoxic agents while at the doses studied Compounds A, F and G appear to be slightly more active than sodium di-n-propylacetate.

III. Anticonvulsant activity

This test is carried out on mice with a view to determining whether the compounds of this invention, when given preventively by intraperitoneal route, are capable at certain doses of protecting some of the animals against the epileptic seizure produced by an adequate and predetermined dose of pentylenetetrazol which would be 100% fatal in the absence of the compound.

The test was carried out on batches of 10 mice. Each batch of animals received an intraperitoneal dose of the compound to be studied so that each batch received a higher dose than the preceding batch. Fifteen minutes after administration of the compound to be tested, the animals were each given 125 mg/kg of pentylenetetrazol by intraperitoneal route. The percentage of deaths was noted 3 hours after injection of this latter compound and the result was expressed as a percentage of protection.

The results obtained with compounds of the invention are given in the following Table:

TABLE III

| Compound | Dose administered in mg/kg | % of protection |
|---|---|---|
| A | 160 | 100 |
| B | 175 | 85 |
| C | 185 | 85 |
| F | 185 | 95 |
| G | 175 | 75 |

A comparative trial performed with sodium di-n-propylacetate under the same conditions showed that a dose of 250 mg/kg of this product protects 100% of the animals against the pentylenetetrazol-induced seizure.

These results indicate that Compounds A and F are more active, in this test, than sodium di-n-propylacetate.

As against this, it was observed that Compounds B and C exert their action over a longer period of time than sodium di-n-propylacetate.

Thus, 195 mg/kg of Compound B and 210 mg/kg of Compound C both of which offer about 100% protection against the pentylenetetrazol-induced seizure, still protect 40% and 70% respectively of the animals one hour after administration.

As against this, a dose of 250 mg/kg of sodium di-n-propylacetate only offers, in this test, 20% protection of the animals, one hour after administration.

Furthermore, additional trials performed with compounds of the invention in accordance with the process described hereabove have shown that a dose of Compound A as low as 105 mg/kg administered by intraperitoneal route, offers 85% protection against the pentylenetetrazol-induced seizure.

Similarly, it was found that a dose of 125 mg/kg of Compound C, also administered by intraperitoneal route, protects 65% of the mice against the pentylenetetrazol-induced seizure.

IV Acute toxicity

Acute toxicity was determined on the mouse. For this purpose, a dose of the compound to be tested was administered to batches of 5 mice, by intraperitoneal route, so that each batch received a higher dose than the preceding batch.

The following results were registered with the compounds of the invention:

| Compounds | $LD_{50}$ in mg/kg |
|---|---|
| A | 500 |
| B | 350 |
| C | 350 |

-continued

| Compounds | LD$_{50}$ in mg/kg |
|---|---|
| F | 300 |

Furthermore, the LD$_0$ of Compounds A and D, namely the maximum tolerated dose (M.T.D.) or the highest dose which provokes no deaths amongst the trial animals was found to be greater than 400 mg/kg, by intraperitoneal route, in the mouse.

It will be appreciated that for therapeutic use the compounds of the invention will normally be administered in the form of a pharmaceutical or veterinary composition in a dosage unit form appropriate to the required mode of administration, the composition comprising as active ingredient at least one compound of the invention in association with a pharmaceutical carrier or excipient therefor. For oral administration, the composition may take the form of, for example, a coated or uncoated tablet, a hard- or soft-gelatin capsule, a suspension or a syrup. The composition may alternatively take the form of a suppository for rectal administration, or of a solution or suspension for parenteral administration.

When in dosage unit form, the composition may contain from 200 to 500 mg of active ingredient per dosage unit for oral administration, from 400 to 1000 mg of active ingredient per dosage unit for rectal administration, or from 100 to 400 mg of active ingredient for parenteral administration.

The therapeutic compositions of the invention will be prepared by associating at least one of the compounds of formula I or a pharmaceutically acceptable alkali metal salt thereof with at least one appropriate carrier or excipient therefor. Examples of suitable carriers or excipients are talc, magnesium stearate, lactose, saccharose, colloidal silica, carboxymethylcellulose, starches, kaolin, levilite, mannitol, cocoa butter.

The following Examples illustrate the preparation of the compounds of the invention together with suitable therapeutic compositions:

EXAMPLE 1

Preparation of 3-n-propyl-hexanoic acid a. 3-n-Propyl-3-hydroxy-hexanoic acid

In a 3-necked flask, a ionic radical solution was prepared by mixing 128 g (1 mol) of naphtalene, 6.9 g (1 mol) of lithium and 600 ml of tetrahydrofuran for 3 to 4 hours. The mixture was then cooled to between −10° and −15° C and 30 g (0.5 mol) of acetic acid for metalation dissolved in the same volume of tetrahydrofuran were added drop by drop. The reaction mixture was heated to about 50°–60° C for 90 minutes. The dianion so formed was brownish-coloured. This mixture was then quickly added to 57 g (0.5 mol) of 4-heptanone dissolved in 250 ml of anhydrous ether. The mixture so formed was refluxed for 90 minutes and then hydrolysed with a minimum of water. The alkaline layer was decanted and acidified. It was then extracted with ether, dried over anhydrous sodium sulphate and filtered. The ether was evaporated out and the residue was distilled.

In this manner, 49.6 g of 3-n-propyl-3-hydroxy-hexanoic acid were obtained in the form of a viscous liquid.

Yield: 59%

B.P. 108°–110° C under 0.25 mmHg.

By following the same procedure as that described above but using the appropriate starting-products, the compounds listed hereunder were prepared:

| Compound | |
|---|---|
| 3-Ethyl-3-hydroxy-pentanoic acid (yield : 52%) | used in crude form |
| 3-n-Butyl-3-hydroxy-heptanoic acid (yield : 35%) | used in crude form | b. 3-n-Propyl-hexanoic acid

The 3-n-propyl-3-hydroxy-hexanoic acid, obtained above, was refluxed in a flask with 248 g of acetic anhydride (1 g of acid for 5 g of anhydride) for 120 to 150 minutes. After this period of time, the anhydride in excess was eliminated by means of a rotating evaporator. The mixture of ethylenic acids so obtained was mixed with 100 ml of distilled water for 30 to 60 minutes by heating under reflux. The mixture was then extracted with ether. The ethereal phases were dried over anhydrous sodium sulphate and the filtrate was evaporated. The residue so obtained, which was composed of the mixture of the isomeric acids was distilled and the higher fraction was eliminated. The new residue so obtained was formed with a mixture of 3-n-propyl-2-hexenoic and 3-n-propyl-3-hexenoic acids. Then 15.6 g (0.1 mol) of the mixture of isomeric ethylenic acids dissolved in 150 ml of absolute ethanol were placed in a bomb-apparatus maintained at a temperature of 100° C for 10 hours, under a pressure of 100 kg/cm$^2$ and the presence of about 10 g of Raney's nickel (i.e. a finely divided nickel catalyst obtained by dissolving out with alkali the aluminium from a nickel-aluminium alloy). After cooling, the reaction mixture was filtered, the alcohol evaporated off and the residue was distilled.

In this manner, 9.6 g of 3-n-propyl-hexanoic acid were obtained in the form of a colourless, slightly viscous liquid, insoluble in water and soluble in the organic solvents.

Yield: 55% calculated from the mixture of ethylenic acids.

B.P. 131° C under 15 mmHg.

By following the same procedure as that described hereabove, but with hydrogenation periods up to 20 hours and using the appropriate starting-products, the following compounds were prepared :

| Compound | Boiling point in ° C |
|---|---|
| 3-Methyl-butanoic acid | 176 (760 mmHg) |
| 3-Ethyl-pentanoic acid | 85–87 (1 mmHg) |
| 3-n-Butyl-heptanoic acid | 130 (4 mmHg) |
| 3-Methyl-pentanoic acid | 196–200 (760 mmHg) |

EXAMPLE 2

Preparation of 5-n-propyl-octanoic acid a. 5-n-Propyl-octanol

In a flask, 150.4 g (0.8 mol) of 5-n-propyl-1,5-octanediol (B.P. 142°–144° C under 3 mmHg) were refluxed with 400 ml of acetic anhydride for 3 hours. The acetic acid so formed and the acetic anhydride in excess were distilled off and the residue so formed was refluxed for a further 30 minutes. The acetyl derivative so obtained was then hydrogenated at room-temperature and in glacial acetic acid to which palladium/barium sulphate had been added. The reaction mixture was then filtered. The 5-n-propyl-1-octyl acetate (B.P. 108°–110° C under 3 mmHg) contained in the filtrate was then saponified by adding a methanolic solution of potassium hydroxide.

In this manner, 5-n-propyl-octanol was obtained boiling at 105° C under 0.1 mmHg.

b. 5-n-Propyl-octanoic acid

In a flask, 86 g (0.5 mol) of the 5-n-propyl-octanol obtained above, were added drop by drop to a previously cooled solution of 191 g of chromic anhydride in 1.7 l of glacial acetic acid containing 195 ml of water, care being taken to maintain the mixture at a temperature of 10° C maximum. The reaction medium was then allowed to stand for about 2 hours at 0° C and 24 hours at room-temperature. After this time, 8.5 l of water were added and the mixture was extracted with chloroform.

In this manner, 5-n-propyl-octanoic acid was obtained boiling at 136° C under 3 mmHg.

By following the same procedure as that described above but using the appropriate starting-products, the compounds hereunder were prepared:

| Compound | Boiling point ° C |
| --- | --- |
| 4-Methyl-pentanoic acid | 197 (750 mmHg) |
| 4-n-Propyl-heptanoic acid | 106–107 (1 mmHg) |

EXAMPLE 3

Preparation of 3-n-propyl-2-hexenoic acid

In a flask, 15.6 g (0.1 mol) of 3-n-propyl-hexanoic acid, obtained as in Example 1, was refluxed for 120 to 150 minutes in 78 g of acetic anhydride (1 g of acid for 5 g of anhydride). At the end of this time, the excess of acetic anhydride was removed by means of a rotating evaporator and the mixture of isomeric ethylenic acids was distilled. The fraction which distilled at 110° C under a pressure of 0.6 mmHg was cooled to between −30 and −40° C and the resulting acid cristallized. It was quickly filtered.

In this manner, 3-n-propyl-2-hexenoic acid was obtained, melting at 20° C.

EXAMPLE 4

Preparation of sodium 4-n-propyl-heptanoate

In a flask, 17.2 g (0.1 mol) of 4-n-propyl-heptanoic acid, prepared as described in the above Example 2, were dissolved in a sufficient volume of water. After that 4 g (0.1 mol) of a sodium hydroxide solution in water were added and the mixture was evaporated to dryness. The residue so obtained was rinsed with ethyl ether and maintained in a dessicator under vacuum.

In this manner, sodium 4-n-propyl-heptanoate was obtained. This product does not melt but decomposes when heated.

Following the same procedure as that described above, the compounds hereunder were prepared:

Compounds

Sodium 3-n-propyl-hexanoate
Sodium 5-n-propyl-octanoate

EXAMPLE 5

Tablets containing the following ingredients were prepared in accordance with known pharmaceutical techniques:

| Ingredients | mg per tablet |
| --- | --- |
| Sodium 4-n-propyl-hexanoate | 200 |
| Mannitol | 138 |
| Corn starch | 120 |
| Colloidal silica | 24 |
| Magnesium stearate | 18 |
| | 500 |

EXAMPLE 6

A suppository containing the following ingredients was prepared in accordance with known pharmaceutical techniques:

| Ingredients | mg |
| --- | --- |
| 4-n-Propyl-hexanoic acid | 400 |
| Glycocoll | 200 |
| Cocoa butter | 1 600 |
| | 2 200 |

We claim:

1. A pharmaceutical or veterinary composition having a competitive inhibitory activity with respect to γ-aminobutyric α-ketoglutaric transaminase and antianoxic and anticonvulsant action comprising as an essential active ingredient at least one acetic acid derivative of the general formula:

$$R-\overset{O}{\underset{\|}{C}}-OH$$

wherein R is $$\begin{array}{c} R_1 \\ \diagdown \\ \diagup \\ R_2 \end{array} CH-(CH_2)_n-\underset{R_3}{CH-} \quad \text{or} \quad \begin{array}{c} R_1 \\ \diagdown \\ \diagup \\ R_2 \end{array} C=CH-$$

in which $R_1$ and $R_2$, which may be the same or different, each represent an alkyl radical having from 1 to 4 carbon atoms, $R_3$ represents a hydrogen atom or a methyl radical and $n$ is an integer in the range of from 0 to 3 inclusive, or a pharmaceutically acceptable alkali metal salt of the said derivative, in association with a pharmaceutical carrier or excipient therefor, in dosage unit form containing from 100 to 1000 milligrams of active ingredient per unit.

2. A pharmaceutical or veterinary composition having a competitive inhibitory activity with respect to γ-aminobutyric α-ketoglutaric transaminase and antianoxic and anticonvulsant actions comprising as an essential active ingredient 3-n-propyl-hexanoic acid or a pharmaceutically acceptable alkali metal salt thereof, in association with a pharmaceutical carrier or excipient therefor, in dosage unit form containing from 100 to 1000 milligrams of active ingredient per unit.

3. A pharmaceutical or veterinary composition having a competitive inhibitory activity with respect to γ-aminobutyric α-ketoglutaric transaminase and antianoxic and anticonvulsant actions comprising as an essential active ingredient 4-n-propyl-heptanoic acid or a pharmaceutically acceptable alkali metal salt thereof, in association with a pharmaceutical carrier or excipient therefor, in dosage unit form containing from 100 to 1000 milligrams of active ingredient per unit.

4. A pharmaceutical or veterinary composition having a competitive inhibitory activity with respect to γ-aminobutyric α-ketoglutaric transaminase and antianoxic and anticonvulsant actions comprising as an essential active ingredient 5-n-propyl-octanoic acid or a pharmaceutically acceptable alkali metal salt thereof, in association with a pharmaceutical carrier or excipient therefor, in dosage unit form containing from 100 to 1000 milligrams of active ingredient per unit.

5. A pharmaceutical or veterinary composition of claim 1 wherein the pharmaceutically acceptable alkai metal salt is the sodium salt.

6. A method of inducing antianoxic and anticonvulsant actions and inducing inhibition of γ-aminobutyric α-ketoglutaric transaminase comprising the administration to a subject in need of such treatment of an effective dose of at least one acetic acid derivative of the general formula:

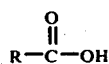

or a pharmaceutically acceptable alkali metal salt thereof, wherein R represents the radical

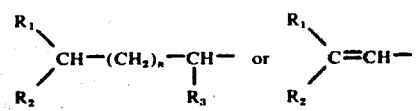

in which $R_1$ and $R_2$, which may be the same or different, each represent an alkyl radical having from 1 to 4 carbon atoms, $R_3$ represents a hydrogen atom or a methyl radical and $n$ is an integer in the range of from 0 to 3 inclusive, said dose being in dosage unit form containing from 100 to 1000 milligrams of active ingredient.

7. The method of claim 6 wherein the acetic acid derivative is 3-n-propyl-hexanoic acid or a pharmaceutically acceptable alkali metal salt thereof.

8. The method of claim 6 wherein the acetic acid derivative is 4-n-propyl-heptanoic acid or a pharmaceutically acceptable alkali metal salt thereof.

9. The method of claim 6 wherein the acetic acid derivative is 5-n-propyl-octanoic acid or a pharmaceutically acceptable alkali metal salt thereof.

10. The method of claim 6 wherein the anticonvulsant action is antiepileptic.

11. The method of claim 6 wherein the human dosage of the acetic acid derivative is between 400 and 2000 mg. per 60 kg. per day.

12. The method of claim 6 wherein the acetic acid derivative is 4-n-propylheptanoic acid or a pharmaceutically acceptable alkali metal salt thereof.

13. The method of claim 6 wherein the acetic acid derivative is 3-n-propylhexanoic acid or a pharmaceutically acceptable alkali metal salt thereof.

* * * * *